(12) United States Patent
Besselink

(10) Patent No.: US 11,241,557 B2
(45) Date of Patent: *Feb. 8, 2022

(54) FLEXIBLE AND STEERABLE DEVICE

(71) Applicant: Petrus A. Besselink, Enschede (NL)

(72) Inventor: Petrus A. Besselink, Enschede (NL)

(*) Notice: Subject to any disclaimer, the term of this patent is extended or adjusted under 35 U.S.C. 154(b) by 244 days.

This patent is subject to a terminal disclaimer.

(21) Appl. No.: 16/566,342

(22) Filed: Sep. 10, 2019

(65) Prior Publication Data

US 2020/0038630 A1 Feb. 6, 2020

Related U.S. Application Data

(63) Continuation of application No. 15/756,729, filed as application No. PCT/IB2016/001347 on Sep. 2, 2016, now Pat. No. 10,441,746.

(Continued)

(51) Int. Cl.
*A61M 25/01* (2006.01)
*A61M 25/04* (2006.01)
(Continued)

(52) U.S. Cl.
CPC ....... *A61M 25/0054* (2013.01); *A61B 1/0056* (2013.01); *A61B 18/24* (2013.01);
(Continued)

(58) Field of Classification Search
CPC . A61B 1/0056; A61B 18/24; A61B 2017/003; A61B 2017/00305;
(Continued)

(56) References Cited

U.S. PATENT DOCUMENTS 3,692,029 A 9/1972 Adair
4,215,703 A 8/1980 Willson
(Continued)

FOREIGN PATENT DOCUMENTS

EP 1684842 A2 8/2006
JP 5113386 A 2/1976
WO 2014077881 A1 5/2014

OTHER PUBLICATIONS

Office Action dated May 4, 2018 in reference to co-pending European Patent Application No. 16787551.7.
(Continued)

*Primary Examiner* — Ryan J. Severson
(74) *Attorney, Agent, or Firm* — Dinsmore & Shohl, LLP

(57) ABSTRACT

A device, a method of making a device and a method of inserting a device into a tubular path. The device includes a tubular sheath with one or more helical slots formed therein and a control element that fits within the sheath. In one form, the device is an endoluminal device that simultaneously improves flexibility and structural rigidity though variations in one or both of slot width along the length of the slot and slot pitch along the length of the tubular sheath. When the operator pulls at the proximal end of the control element while holding the outer sheath in place, the slots will tend to close in a preferential manner such that more precise control of device length and bending is enabled, while simultaneously providing improvements in structural rigidity during device insertion and navigation through a body lumen or related tubular member where tortuous paths may be encountered along the member path.

19 Claims, 7 Drawing Sheets

Related U.S. Application Data

(60) Provisional application No. 62/214,379, filed on Sep. 4, 2015, provisional application No. 62/322,859, filed on Apr. 15, 2016, provisional application No. 62/362,680, filed on Jul. 15, 2016.

(51) Int. Cl.

| | | |
|---|---|---|
| *A61M 25/00* | (2006.01) | |
| *A61B 1/005* | (2006.01) | |
| *A61B 18/24* | (2006.01) | |
| *A61F 2/88* | (2006.01) | |
| *A61M 25/10* | (2013.01) | |
| *A61M 27/00* | (2006.01) | |
| *A61M 29/00* | (2006.01) | |
| *A61M 25/09* | (2006.01) | |
| *A61B 17/00* | (2006.01) | |
| *A61B 18/00* | (2006.01) | |
| *A61F 2/01* | (2006.01) | |

(52) U.S. Cl.
CPC ........... *A61F 2/88* (2013.01); *A61M 25/0051* (2013.01); *A61M 25/0053* (2013.01); *A61M 25/0138* (2013.01); *A61M 25/0147* (2013.01); *A61M 25/104* (2013.01); *A61M 27/00* (2013.01); *A61M 29/00* (2013.01); *A61B 17/00234* (2013.01); *A61B 2017/003* (2013.01); *A61B 2017/00309* (2013.01); *A61B 2017/00331* (2013.01); *A61B 2017/00867* (2013.01); *A61B 2018/00577* (2013.01); *A61F 2002/016* (2013.01); *A61M 25/04* (2013.01); *A61M 25/09041* (2013.01); *A61M 2025/0063* (2013.01)

(58) Field of Classification Search
CPC ........... A61B 2017/00309; A61B 2017/00318; A61B 2017/00323; A61F 2/88; A61M 2025/0063; A61M 2025/015; A61M 25/0051; A61M 25/0053; A61M 25/0054; A61M 25/0105; A61M 25/0133; A61M 25/0136; A61M 25/0138; A61M 25/0147; A61M 25/04; A61M 25/09041; A61M 25/104; A61M 27/00; A61M 29/00
See application file for complete search history.

(56) References Cited

U.S. PATENT DOCUMENTS

| | | | |
|---|---|---|---|
| 5,178,158 | A | 1/1993 | De Toledo |
| 5,217,465 | A | 6/1993 | Steppe |
| 5,330,497 | A | 7/1994 | Freitas et al. |
| 5,397,304 | A | 3/1995 | Truckai |
| 5,741,429 | A | 4/1998 | Donadio et al. |
| 5,769,871 | A | 6/1998 | Mers Kelly et al. |
| 5,807,354 | A | 9/1998 | Kenda |
| 5,848,986 | A | 12/1998 | Lundquist et al. |
| 5,931,830 | A | 8/1999 | Jacobsen et al. |
| 6,004,279 | A | 12/1999 | Crowley et al. |
| 6,136,016 | A | 10/2000 | Barbut et al. |
| 6,355,051 | B1 | 3/2002 | Sisskind et al. |
| 6,468,291 | B2 | 10/2002 | Bates et al. |
| 6,511,471 | B2 | 1/2003 | Rosenman et al. |
| 6,511,496 | B1 | 1/2003 | Huter et al. |
| 6,585,718 | B2 | 7/2003 | Hayzelden et al. |
| 6,599,254 | B2 | 7/2003 | Winters |
| 6,623,448 | B2 | 9/2003 | Slater |
| 6,632,197 | B2 | 10/2003 | Lyon |
| 6,648,875 | B2 | 11/2003 | Simpson et al. |
| 6,673,042 | B1 | 1/2004 | Samson et al. |
| 6,726,701 | B2 | 4/2004 | Gilson et al. |
| 6,755,794 | B2 | 6/2004 | Soukup |
| 6,776,765 | B2 | 8/2004 | Soukup et al. |
| 6,890,329 | B2 | 5/2005 | Carroll et al. |
| 7,097,651 | B2 | 8/2006 | Harrison et al. |
| 7,141,024 | B2 | 11/2006 | Gaber |
| 7,776,062 | B2 | 8/2010 | Besselink et al. |
| 7,998,132 | B2 | 8/2011 | Gregorich et al. |
| 8,092,483 | B2 | 1/2012 | Galdonik et al. |
| 8,303,570 | B2 | 11/2012 | Gregorich et al. |
| 8,382,786 | B2 | 2/2013 | Besselink et al. |
| 8,663,196 | B2 | 3/2014 | Kassab et al. |
| 8,814,848 | B2 | 8/2014 | Gregorich et al. |
| 9,649,473 | B2 | 5/2017 | Gregorich et al. |
| 10,029,071 | B2 | 7/2018 | Hannon et al. |
| 10,188,832 | B2 | 1/2019 | Salahieh et al. |
| 2002/0082585 | A1 | 6/2002 | Carroll et al. |
| 2002/0095102 | A1 | 7/2002 | Winters |
| 2003/0045898 | A1 | 3/2003 | Harrison et al. |
| 2003/0069522 | A1 | 4/2003 | Jacobsen et al. |
| 2004/0059257 | A1 | 3/2004 | Gaber |
| 2004/0092845 | A1 | 5/2004 | Gaber |
| 2005/0085771 | A1 | 4/2005 | Lyon |
| 2005/0113862 | A1 | 5/2005 | Besselink et al. |
| 2006/0089569 | A1 | 4/2006 | Soukup et al. |
| 2006/0116757 | A1 | 6/2006 | Lashinski et al. |
| 2006/0200047 | A1 | 9/2006 | Galdonik et al. |
| 2007/0060880 | A1 | 3/2007 | Gregorich et al. |
| 2007/0233040 | A1 | 10/2007 | Macnamara et al. |
| 2009/0157048 | A1 | 6/2009 | Sutermeister et al. |
| 2010/0076405 | A1 | 3/2010 | Kassab et al. |
| 2011/0196410 | A1 | 8/2011 | Besselink et al. |
| 2011/0301574 | A1 | 12/2011 | Gregorich et al. |
| 2013/0096535 | A1 | 4/2013 | Gregorich et al. |
| 2015/0196732 | A1 | 7/2015 | Gregorich et al. |
| 2015/0297863 | A1 | 10/2015 | Hannon et al. |
| 2019/0060612 | A1 | 2/2019 | Besselink |

OTHER PUBLICATIONS

International Search Report and Written Opinion dated Apr. 20, 2017 pertaining to International Application No. PCT/1B2016/001347.

International Preliminary Report on Patentability dated Dec. 20, 2017 pertaining to International Application No. PCT/1B2016/001347.

International Search Report and Written Opinion, dated Apr. 11, 2017, pertaining to PCT/182016/001347 filed Sep. 2, 2016.

International Preliminary Report on Patentability, dated Dec. 20, 2017, pertaining to PCT/182016/001347 filed Sep. 2, 2016.

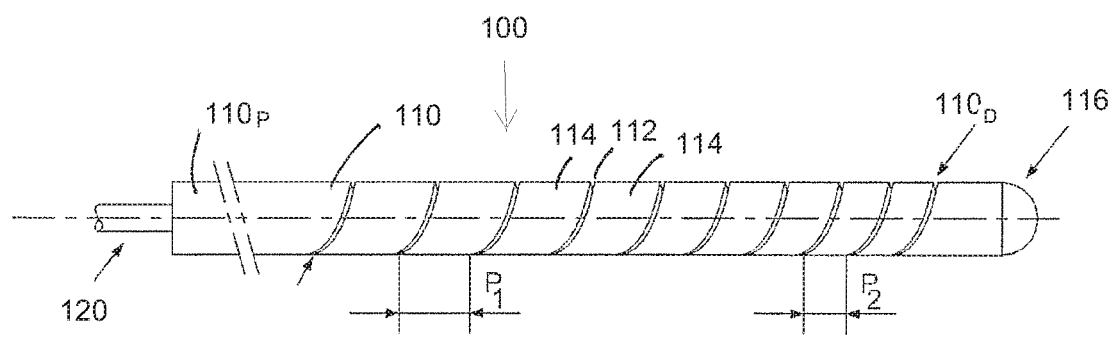
Fig. 7
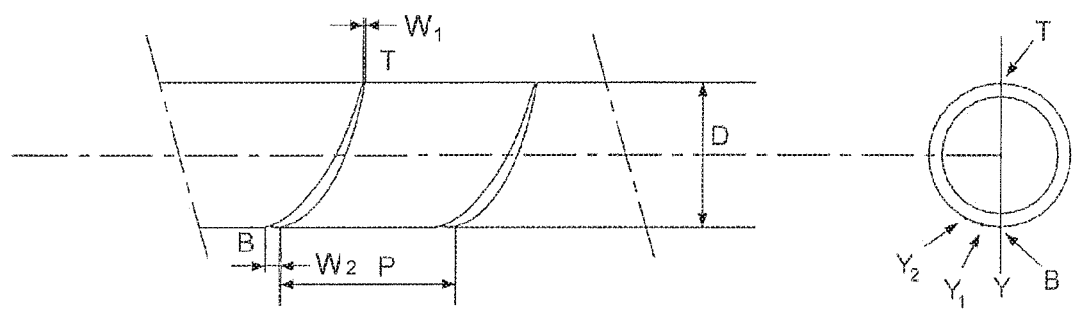
Fig. 8                                       Fig. 9
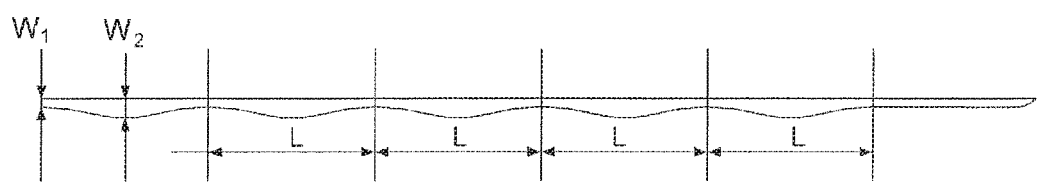
Fig. 10
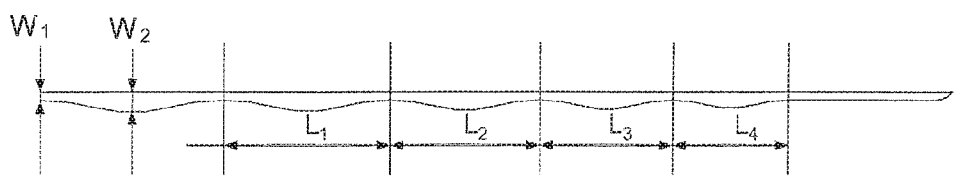
Fig. 11

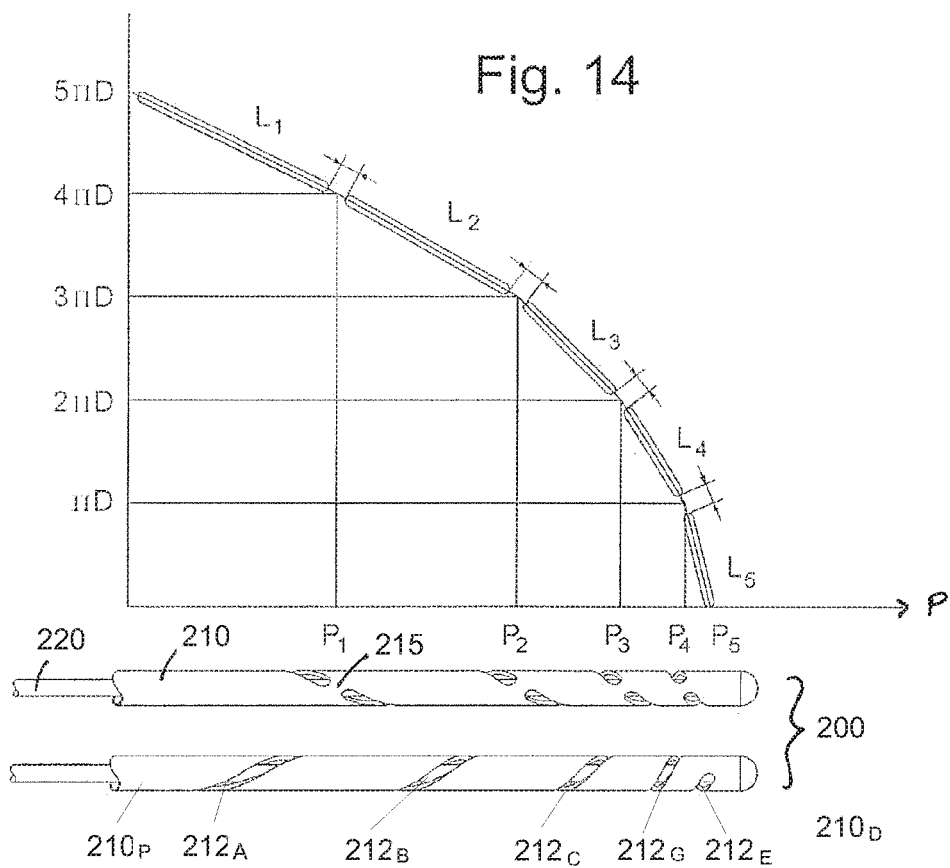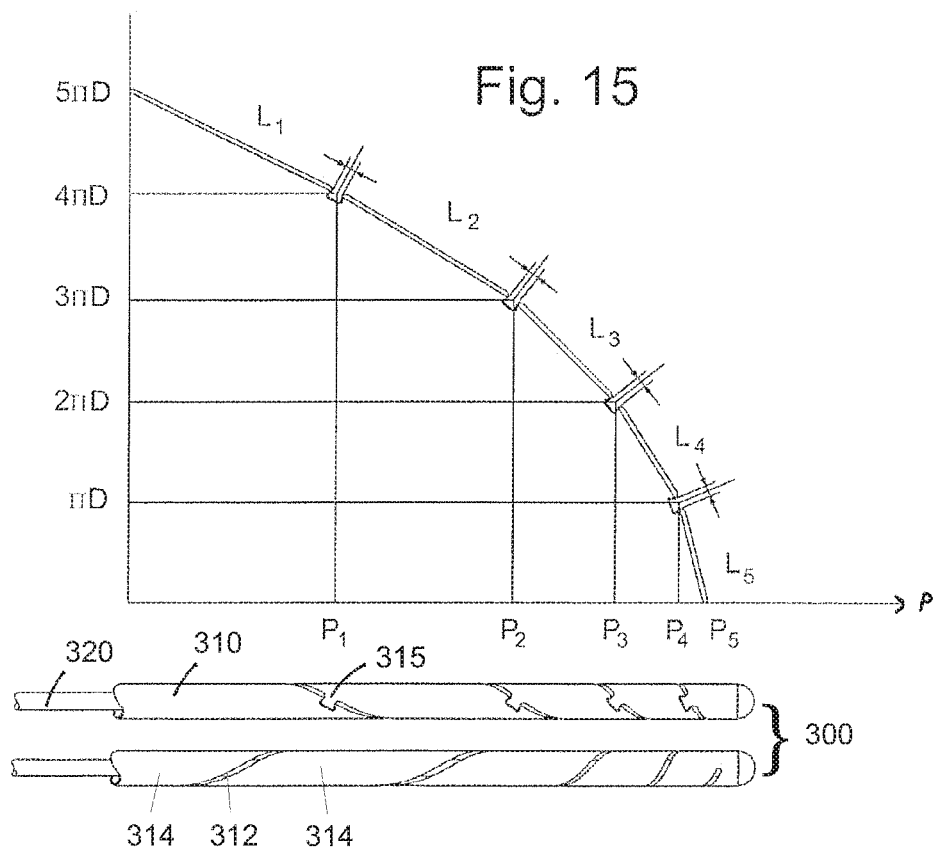

FLEXIBLE AND STEERABLE DEVICE

CROSS-REFERENCE TO RELATED APPLICATION

This application is a continuation application of U.S. patent application Ser. No. 15/756,729 filed Mar. 1, 2018 that is a US National Stage entry of International Application No. PCT/IB2016/001347 filed Sep. 2, 2016, the entire disclosure of which is hereby incorporated herein by reference.

BACKGROUND OF THE DISCLOSURE

The present disclosure relates generally to devices that are inserted into the inner space of tubular members, and in particular to devices that have improved steerability features as a way to improve insertion into and movement within such members.

In general, there are numerous circumstances where a thin, elongate device must be inserted into a lengthy, narrow and often curved or branched tubular member in order to effect navigation and related repair, insertion or other complex activities associated with the device. With particular regard to minimally-invasive medical procedures, there is a need for flexible and steerable guide wires (also referred to herein as guide wire assemblies), stylets, catheters and related devices that generally have to be maneuvered through tortuous body lumens through one or more of pushing, pulling and tangential rotation, and more particularly do so by transferring such movements initiated at the proximal end of the device as accurately as possible to the distal end. While conventional guide wire assemblies with a steerable tip are known in the art as a way to achieve some degree of maneuverability, all have some form of drawback.

For example, some steerable devices have a shapeable tip at the distal end that can be bent to a desired angle before insertion. While the angle enables the operator to maneuver the device into side arteries or related branches in a body lumen, its relatively fixed nature means that once inserted, the tip angle cannot be changed, thereby limiting its subsequent mobility. To overcome the problems associated with such a fixed configuration, other devices have been developed to provide for a measure of remotely controlled steerability, such as by hand manipulation and related user actuation at the proximal end of the device. In one such example as shown by U.S. Pat. No. 6,599,254, the operator pulls a tension wire relative to the guide wire, so that the tip will bend in an amount that varies with the pulling force. In another example, U.S. Pat. No. 5,741,429 uses a hollow guide wire with a series of slots made in the tubular member wall at the place where more flexibility is desired. Relatedly, US Patent Application Publication 2003/0069522 shows that numerous pairs of slots are cut into the body to make it more flexible in bending while maintaining adequate torsional stiffness, while US Patent Application Publication 2004/0059257 shows numerous radial slots—all with the same cut depth—formed near the tip distal end, with the distance between the slits increasing farther away from the distal tip. In yet another example, U.S. Pat. No. 6,776,765 varies the depth of the slots over the length, with the deepest slots near the distal end, while keeping the axial distance between the slots identical, possibly in an attempt to vary the rigidity of the remaining tubular member material with slot depth. In still another example, U.S. Pat. No. 6,623,448 shows a device with an alternating pattern of opposing slots defined by a small linear offset; while such a configuration provides enhanced flexibility upon bending, the steerability is compromised, while manufacturing costs tend to be high. More significantly, fracture of the fragile wall near any slot causes complete failure of the device.

Helical slots have been proposed in an attempt to promote flexibility; however, it is difficult to achieve a reliable, repeatable one-to-one correspondence between the initiated rotation at the proximal end and the responsive rotation at the distal end. By way of example, U.S. Pat. No. 6,755,794 shows a single helical cut formed in the tubular member. The helix has an invariable pitch, and upon pulling the control wire, the gaps in the outer sheath all close at the same time, which in turn requires the device to remain straight regardless of whether the gaps are opened or closed. Such construction means that the only thing be varied is the rigidity of the device, so while a conventional helical cut can provide the selective flexibility needed to provide ample degrees of steerability, it has proven to be a vexing problem to use such cuts to keep a good reliable one to one rotational movement between proximal and distal ends.

In addition to steerability concerns, manufacturability issues must be addressed, especially where the device is meant for endoluminal use. In particular, as can be seen from the foregoing examples, normally laser cutting or similar techniques are used to form a pattern of slots into the wall of a tubular member. Such techniques (which often result in localized heating during the cutting process) tend to weaken the remaining material around the slot. This problem manifests itself during bending operations where elevated stress tends to be concentrated in a very localized region, leading to an increased risk of breakage in such region. The present Applicant believes that there is not enough remaining unharmed base material to absorb these stresses while the device is introduced and maneuvered into a tortuous path such as a body lumen. To overcome this elevated local stress problem, other approaches, such as that of U.S. Pat. No. 5,931,830 have been developed, where the member is produced by forming a strip of material into an elongate helical coil. Additional locks are used to improve the torsional stability, and while such an approach helps avoid or reduce the stress problems associated with traditional slot formation, the high costs render such approaches prohibitive, as does the inability to simultaneously control bending along with the increased torsional stability.

SUMMARY OF THE DISCLOSURE

According to one aspect of the present disclosure, a steerable device is disclosed. The device includes a tubular sheath and an elongate control element disposed within and attached to the tubular sheath. The sheath has a proximal end, a distal end and one or more reconfigurable sections disposed between these two ends. Within at least the reconfigurable section, one or more helical slots may be formed through the sheath wall. In addition, the one or more slots may include a variable slot width, a constant or variable slot pitch or both. By having variations in one or both of the slot width and pitch, an operator-induced axial force applied to the elongate control element can be used to cause the variation in the slot to produce at least one of a change of the flexibility, rotatability or pushability, rotation of the distal section and a distal end bending within the tubular sheath.

According to another aspect of the present disclosure, a medical device for use in a body lumen is disclosed. The medical device includes an elastic bias section disposed proximal relative to a tubular sheath and elongate control element that cooperate with one another to provide a steerable section where device bending and rotation may be implemented. The elastic bias section can be used by a physician or related operator to vary the shape of the tubular sheath through changes in length that result from an axial force imparted to the elongate control element. In one form, the medical device is a guide wire assembly such that the elongate control element is a wire such that the elastic bias section forms a tool through which the operator may manipulate the wire. Additional portions of the device may include an intermediate section and an anchoring section to selectively provide secure contact between the device and a body lumen interior wall.

According to another aspect of the present disclosure, a method of using a steerable device is disclosed. The method includes positioning the device within a tubular path and moving the device within the tubular path such that when a distal end (such as the tip of a reconfigurable section that has at least one of bendability and rotatability attributes) of the device reaches a bend, bifurcation or other change in direction within the tubular path, the distal end may be reconfigured in order to be steerably moved through the bent, bifurcated or changed region. The device includes a tubular sheath defining a proximal end, a distal end and at least one reconfigurable section disposed between the proximal and distal ends. The tubular sheath also includes one or more helical slots formed through the sheath wall. The one or more slots are constructed so that they possess either or both of variable slot width and a constant or variable slot pitch along the length of the reconfigurable section at least while the tubular sheath is in a substantially undeformed shape. An elongate control element is cooperative with the tubular sheath such that upon application of an axial force to the elongate control element, one or both of the variable slot width and the constant or variable slot pitch to produce at least one of a change of the flexibility, rotatability or pushability, rotation of the distal section and a distal end bending within the tubular sheath.

BRIEF DESCRIPTION OF THE SEVERAL VIEWS OF THE DRAWINGS

The following detailed description of the present disclosure can be best understood when read in conjunction with the following drawings:

FIG. 7 shows a section of a helically-slotted tubular sheath portion of a guide wire assembly according to another embodiment of the present disclosure;

FIG. 8 shows a detail view of the helically-slotted tubular sheath;

FIG. 9 shows a section cut view of the helically-slotted tubular sheath of FIGS. 7 and 8;

FIG. 10 shows periodically-varying thicknesses of a length of material that could be used to make up a tubular sheath portion of a guide wire assembly according to an embodiment of the present disclosure, where the pitch between adjacent slot sections is constant;

FIG. 11 shows periodically-varying thicknesses of a length of material that could be used to make up a tubular sheath portion of a guide wire assembly according to an embodiment of the present disclosure, where the pitch between adjacent slot sections varies along the axial length of the tubular sheath;

FIG. 14 shows three views of a section of a helically-slotted tubular sheath portion of a guide wire assembly according to another embodiment of the present disclosure;

FIG. 15 shows three views of a section of a helically-slotted tubular sheath portion of a guide wire assembly according to another embodiment of the present disclosure.

DETAILED DESCRIPTION

Figure 1:
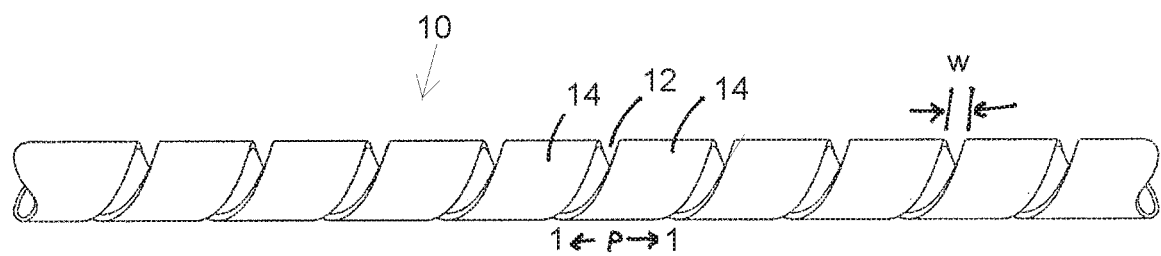
FIG. 1 shows a section of a helically-slotted tubular sheath portion of a guide wire assembly in an axially elongated shape according to the prior art.

Embodiments disclosed herein include a device that can be inserted into and navigated through complex tortuous hollow bodies for various applications, such as body lumens for medical procedures. Such devices may be used in conjunction with other endoluminal devices, including those disclosed in U.S. Pat. Nos. 7,776,062 and 8,382,786, as well as European Patent 1,684,842 and Japanese Patent 5,113,386, all of which are incorporated herein by reference in their entirety. The device disclosed herein may also be used for non-medical procedures, such as those associated with exploration, completion and maintenance of oil, gas and water wells, fluid and gas transport systems. Devices according to the present disclosure exhibit greater reliability in part because their construction avoids many of the fracture and related breakage problems associated with traditional devices, while also improving on ease of manufacture.

As will be discussed in more detail herein, the device of the present disclosure provides increases in both flexibility and steerability while preserving the structural rigidity necessary to ensure the reliable, repeatable correlation between controlling movement at one elongate end of the device and rotational movement at the opposing end of such device. Several main features as discussed in more detail below may be used singly or in conjunction with one another to contribute to simultaneously meeting these competing objectives. These features include the fact that (1) axially-induced tension causes bending in a slotted helical tube that has a variable slot width, (2) locking members and hinges may be used to prevent undesirable torque loss in slotted helical tube situations where a rotation initiated at one end is meant to be transferred one-to-one to the other end, and (3) axially-induced tension causes torque in a slotted helical tube in what is referred to as self-torque-tip (STT) so that a device section rotates tangentially around its own length axis in response to an applied length change in a helical wall due to such tension. Within the present context, this last feature pertains to a helical section that rotates tangentially around its own length axis by applying a length change in the helical wall. STT depends on various structural considerations of the helix, including pitch angle of the helix and sheath wall thickness.

Embodiments disclosed herein can take advantage of these features to meet the long-felt needs mentioned above. As will be discussed in more detail below, in one form, a device made up of at least a tubular sheath and a control element centrally disposed along the axial dimension of the sheath cooperate with one another such that the control element can impart a preload onto the sheath in such a way to close tangential gaps in locking members that are formed between adjacent wall sections of the sheath. By closing these gaps, a controllable reduction in sheath floppiness can be realized, which in turn results in an improved tangential stiffness and a higher degree pushability during device insertion into a body lumen or other tubular member. In another form, interrupted helical slots create hinges in the wall of the sheath. As with the locking members mentioned above, such hinges can improve the tangential one-to-one movement that is needed to achieve repeatable rotational stability. In yet another form, the helical slots may have a variable width along their length. Because the width is not everywhere the same, an axial deviation of adjacent sections will form upon application of a force on the sheath through the control element as gaps within the slot will close at different times commensurate with the degree of width variability. In a related form, this bending effect experienced by the variable-width slots also works for helical slot forms with hinged interruptions; for example, where the hinges are situated on the convex side of a tubular sheath, an applied force tends to close the gap on the circumferentially opposing side. With such a configuration, bending may take place in one plane but also in several planes, depending of the position and shape of the slots and their corresponding hinges, interlocking members or the like.

In yet another form, the tangential self-rotation effect—where minor tangential rotation relative to a neighbor coil (also referred to herein as wall section) upon closure or opening of the slot occurs when tension is applied to a helical sheath—may be used advantageously to eliminate the need to have an operator apply tangential rotation at the device proximal end. In this way, mere axial movement of an elongate control element can cause the distal section to start rotating even while the majority of the sheath has yet to start rotating. The fact that only a short section of the wall is rotating reduces the total friction with the inner wall of the lumen in which the device is placed. This in comparison with a conventional device, which has to be rotated over its entire length. Both the accuracy and reduced friction associated with rotational movement thereby improves, especially for endoluminal and other very thin devices that are designed to navigate tortuous paths. As will become apparent from the present disclosure, this latter self-rotation effect can be combined with the locking members or other rotation-inhibition devices as discussed above in order to limit excessive deformation, as well as to control the bending effect caused by variable slot width.

Lastly, in yet another form, the spacing or pitch between axially adjacent portions of the slot at common circumferential positions on the sheath may be varied in order to create a gradual change in stiffness of the device. With such construction, smaller pitch (i.e., more closely-spaced slot portion) sections tend to exhibit more bendability than larger pitch (i.e., farther-spaced slot portion) sections.

Figure 2:
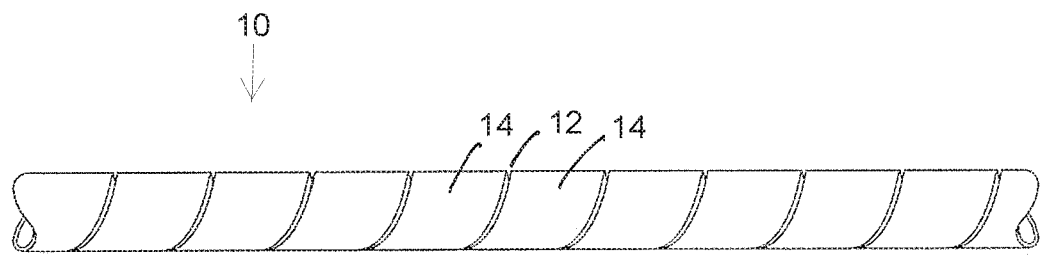
FIG. 2 shows the helical cut tubular sheath of FIG. 1 in its as-cut state, showing smaller slot widths.
Figure 3:
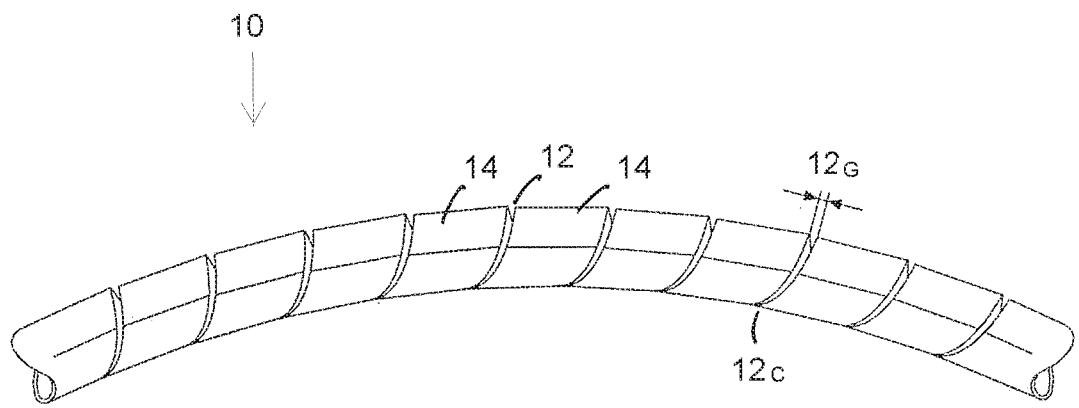
FIG. 3 shows the tubular sheath of FIG. 2 in a bent shape.

Referring first to FIGS. 1 through 3, a reconfigurable section of a tubular sheath 10 with a slot (also referred to herein as a kerf) 12 formed in a wall 14 thereof is shown, where the helical nature of the slot 12 resembles the familiar "barber-pole" pattern. As shown with particularity in FIG. 1, the sheath 10 is in an axially stretched or elongated form, or in its as-cut state with a large slot width where in this latter form the sheath 10 can be used as a compression spring a the proximal end of a guide wire assembly. FIG. 2 shows the sheath 10 in its as-cut dimension, and FIG. 3 shows the sheath 10 bent to define an arcuate path that deviates from the linear shape of FIGS. 1 and 2. Both the pitch P (i.e., the axial dimension spacing between adjacent slot sections at the same circumferential wall position) and the width W of the slot 12 remain constant over the length of the slot 12 while the sheath 10 is in its nominal (i.e., undeformed) axially-aligned configuration of FIGS. 1 and 2. Likewise, upon bending as shown in FIG. 3, relative closures $12_C$ and gaps $12_G$ form between adjacent wall 14 sections; these closures $12_C$ and gaps $12_G$ correspond to reductions and increases in the width W of the slot 12 that are present on the respective concave and convex sides of the sheath 10. As shown, the closures $12_C$ become smaller upon increased bending and finally become zero when the walls 14 of adjacent sections between adjacent slots 12 touch each other. Contrarily, on the convex side, the gaps $12_G$ will increase to be wider than the nominal width W.

Figure 4:
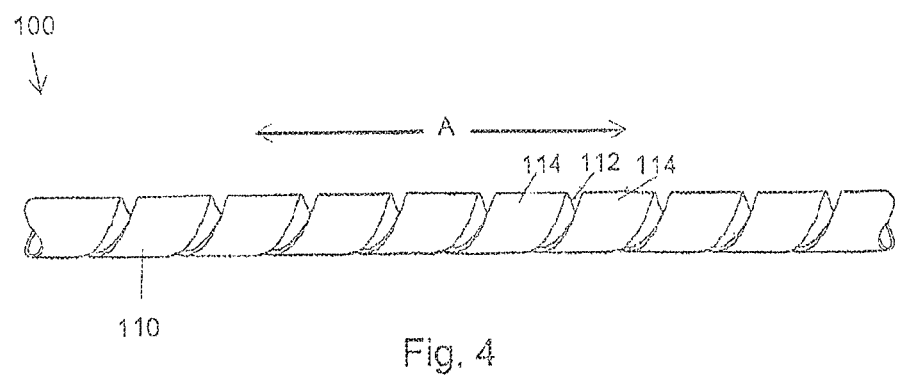
FIG. 4 shows a section of a helically-slotted tubular sheath portion of a guide wire assembly in an axially elongated shape according to an embodiment of the present disclosure.
Figure 5:
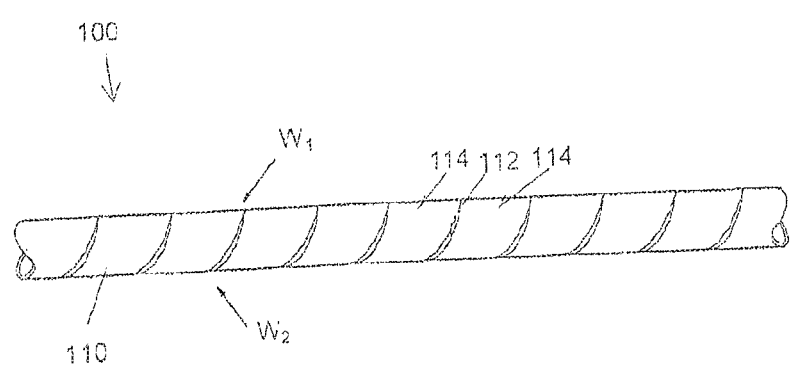
FIG. 5 shows the helical cut tubular sheath of FIG. 4 in its as-cut state, showing variable-width slots.
Figure 6:
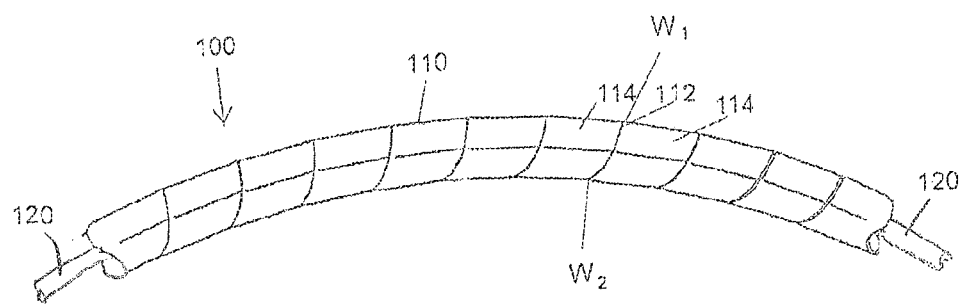
FIG. 6 shows the tubular sheath of FIGS. 4 and 5 in a bent shape, along with the elongate control element used to produce such bending.

Referring next to FIGS. 4 through 6, a reconfigurable section of a tubular sheath 110 according to an embodiment of the present disclosure also has a continuous slot 112 arranged in a helical shape between equally continuous wall 114 where adjacent sections of the wall 114 define the corresponding section of the slot 112. Within the present context, these adjacent wall sections 114 that define the slot 112 between them are also referred to as coil sections commensurate with the helical nature of the tubular sheath 110 construction. In one preferred embodiment, the sheath 110 makes up a portion of an endoluminal device 100 (such as a guide wire assembly), and is shown presently in an axially stretched or elongated form (FIG. 4) that allows the sheath 110 to be used as a compression spring when loaded in its axial direction A. When used as such a device, a notional slot 112 width of about 20 microns or even smaller can be achieved when using nitinol tubing with an outer diameter of 350 microns and wall thickness of about 70 microns where such dimensions are often useful in endoluminal procedures). As is shown with particularity in FIG. 5, and as will be discussed in more detail below, by the present disclosure, the as-cut slot 112 width W (of which the aforementioned 20 microns is an exemplary, rather than limiting, value) can be varied between a minimal width $W_1$ to a maximum width $W_2$. Sheaths 110 according to the present disclosure may be made of metal, polymer, ceramics, metal alloys, alloys with shape memory, linear elastic and/or superelastic behavior (such as nitinol, NiTiNb or related ternary alloys) and all combinations thereof. It is within the scope of the present disclosure that any material or any combination of materials can be used in any of the embodiments discussed herein.

FIG. 6 shows with particularity the sheath 110 in its bent state such as that associated with an axial contraction of the sheath 110 by an internal actuating tension wire (not presently shown). Significantly, upon such bending, there is no substantial variation in the width W of the various slot 112 sections along the length of the sheath 110. As such, the closures $12_C$ and gaps $12_G$ that were present in the bent sheath 10 of the prior art of FIG. 3 are replaced by converging adjacent wall 114 sections such that no open slots remain. In this shape of sheath 110, the borders of the adjacent wall 114 sections are in contact with one another, which in turn causes the sheath 110 to possess a relatively rigid state compared to that of FIG. 3.

Referring next to FIGS. 10 and 11, the tailoring of the width W of the slots 112 of the sheath 110 of FIGS. 4 through 6 can be achieved by using the cutting pattern or template where a generally two-dimensional simulation of the width variations along the length of the helical slot 112 that is formed in wall 114 of sheath 110 can be better visualized. Within the present context, the width W of the slot 112 that is cut into the wall 114 of the sheath 110 is made to vary in a tangential direction around the circumference of the sheath 110. In one form, there is only a single cut formed throughout the entirety of the steerable, flexible section of the sheath 110. When an operator pulls at the proximal end of a central actuation wire (such as that depicted in FIG. 7 below) while he holds the outer tube in place, the slots in the distal section will tend to close. As the slot width varies along the circumference of the slotted cross section, the edges of the smallest slot width in the tube will close earlier than the opposing edges, where the slot is wider. At that moment the device is still straight, but if the central actuation wire is pulled out further, the remaining asymmetrical gap will tend to close and the tube will start bending.

Referring with particularity to FIG. 10, slot 112 is shown with one edge defining the width W in vertical direction and the repeating cutting length L in horizontal direction. Slot 112 width W varies alternating between $W_1$ and $W_2$. When both the rotation speed of the sheath 110 and the axial feed are constant, the length of the cut going in one loop from top to top corresponds to the repeating length L. Within the present context, a loop corresponds to the helical length or section of a slot 112 from one circumferential location on a sheath 110 to the next portion of the sheath 110 at the same circumferential location upon traversal along the slot 112. The value of length L depends on pitch P and diameter D, as explained in conjunction with FIGS. 8 and 9 below in conjunction with FIG. 6. If length L is exactly enough to reach bottom point B for every loop, all points corresponding to the maximum width $W_2$ will be in a straight line that is parallel to the center axis of the sheath 110. In this case all loops have equal lengths L. The resulting sheath 110 resembles that depicted in FIGS. 4 through 6.

Referring with particularity to FIG. 11, where the amplitude of the width W of slot 112 varies again between $W_1$ and $W_2$ but the feed of the sheath 110 is variable, the length L of the cut varies over the length of the sheath 110, thus creating different lengths $L_1$, $L_2$, $L_3$ and so on. This results in different respective pitch values $P_1$, $P_2$, $P_3$ and so on. The resulting sheath 110 resembles that depicted in FIG. 7. By varying the feed of the sheath 110 and the rotation speed, it is also possible to not only vary the pitch P over the length, but also varying the locations of the points where the maximum width $W_2$ is located in a manner similar to that associated with the discussion of FIGS. 8 and 9 for locations Y, $Y_1$ and $Y_2$. Further additional sheath 110 parameters may be varied in order to optimize a design. For example, the variations in slot 112 width need not only be restricted to an alternating pattern of two values for $W_1$ and $W_2$; there may be more widths W used to provide even more flexibility and steering behaviors. Moreover, additional cuts can be tailored to improve only the flexibility, while leaving the steerability the same.

In providing the slot 112 with a variable width, such as by various known techniques including laser cutting, mechanical cutting with fine blades, electrostatic discharge machining (EDM), chemical milling, photo-etching, ablation or the like. Likewise, variations in shapes of the slot 112 may also be formed, such as through using several cuts, using a zigzag cut with variable amplitude, using another offset cut, using a variable cutting energy, using a variable spot size, or winding the helical shape from a strip with variable width. In one form, one end of the sheath 110 may be held in a chuck (not shown) that rotates, while the laser (not shown) is positioned close to and above the rotating sheath 110 surface. Either the sheath 110 moves in axial direction under the laser or the laser moves in axial direction relative to the sheath 110 end In either variant, it is that the cutting pattern varies over the length of the helical slot 112 being formed. In one variation, the spot size of the laser varies, dependant on the angle of rotation of the sheath 110 around its central length axis. The spot size—and thus the amount of removed material—can be varied in order to create a slot 112 that alternates in widths between $W_1$ and $W_2$ for every full rotation of the sheath 110. If the spot size cannot be enlarged fast enough or big enough, the alternative would be to cut a second time over the same slot 112, with some offset at all places where slot 112 enlargement is needed. Alternatively, the slotting speed may be alternately lowered in order to remove more material locally, while a zigzag movement be used to enlarge the slot 112 as well.

Referring again to FIG. 6, the sheath 110 with a cutting pattern as shown in FIG. 5 is axially compressed by the tension in the control element 120, which causes bending of the sheath 110. On the concave side of the bent sheath 110, the width $W_2$ of slot 112 becomes smaller upon increased bending and finally becomes zero when the wall 114 sections on opposing lateral sides of the slot 112 touch each other. Simultaneously on the convex side, the width $W_1$ of slot 112 will also become smaller and decreases further after contact between adjacent wall 114 sections is attained by the reductions in width $W_2$ on the concave side. In fact, a calculation of the total bending angle of sheath 110 can be made as follows. By way of example, a given sheath 110 diameter of D that is bent over an imaginary mandrel with diameter $D_1$ until the sheath 110 is bent over a total angle of 180 degrees. In that final position, all gaps in the concave side are closed, so the length of the convex side is larger than the concave side with a difference of $n\Delta W$ where n is the number of slots. Then the following equations can be used to calculate n. Total length of convex side over 180 degrees is $L_1=(\pi(D_1+D))/2$. Total length of concave side is $L_2=(\pi D_1)/2$. $L_1=L_2+n\Delta W$. This gives $n=\pi D/(2\Delta W)$. For example if $\Delta W=20$ microns and $D=350$ microns, it follows that $n=27.5$ slots 112 for 180 degrees of bending. If the mandrel has a diameter $D_1=10$ mm, the pitch P is then calculated as follows. $P=L_2/n=(\pi D_1)/2n=5\pi/27.5=0.57$ mm. Other sizes can be calculated easily from these formulas. For example, if $D=350$ microns and $\Delta W=20$ microns, then $D_1=2nP/\pi=17.5$ P. Thus, if P is assumed to be 0.8 and n is 12, then $D_1=14$ mm. The bending angle is 180 degrees for 17.5 slots, so in this case the bending angle with all slots closed is then $(12/27.5)180=131$ degrees. It is clear that if $\Delta W=W_2-W_1=20$ microns and if the pitch $P=0.57$ mm, a sheath 110 as shown in FIG. 6 with $D=350$ micron and $n=27.5$ can bend over 180 degrees when all gaps are closed. The diameter $D_1$ will then be 10 mm, while the slots 112 and sheath 110 will resemble FIG. 6.

Referring next to FIG. 7, an endoluminal device 100 according to another embodiment of the present disclosure is shown. In this configuration, a length of sheath 110 surrounds a control wire (also referred to herein as elongate control element) 120 that is attached to the distal tip or end $110_D$ and that extends through the hollow core of the sheath to the proximal end $110_P$, where it can be actuated by some external tool or by a bias spring, such as that of aforementioned U.S. Pat. Nos. 7,776,062 and 8,382,786. Materials making up the control wire 120 may include polymers (including polymers that exhibit one or both of high strength and high modulus of elasticity), as well as metal and metal with enhanced radio-opacity (including magnetic resonance imaging) features. It will be appreciated by those skilled in the art that the control wire 120 may be made from a different material than the sheath 110, and that movement of the control wire 120 may be achieved through a remotely controlled actuator taking advantage of one or more of a shape memory effect, hydraulic pressure, electric or magnetic signal, electromotor, direct, with the assistance of a mechanical gear box, as well as combinations thereof.

The sheath 110 and control element 120 are fixedly attached to one another such that there is equilibrium between a tensile force in the control element 120 and an axial compression force in the wall 114 of the sheath 110. The tensile force is sufficient to bias the endoluminal device 100 in a deformed first shape that can be changed by variation of the tensile force. In changing the tensile force, the endoluminal device 100 assumes a second shape different from the deformed first shape. In the present context, the endoluminal device 100 is considered to exist in a deformed shape when the inherent bias force causes the sheath 110 to assume a shape different than would exhibit in a state of rest if no such force were imposed. For example, with a tension force existing between the control element or wire 120 and the sheath 110, a bend in one or both ends of the device 100 produced by this tension would cause a (preferably elastic) deviation from a normally straight or linear shape along the sheath 110 axial dimension. In such case, the bent shape is considered deformed. Similarly, radial or related outward expansion of the sheath 110 caused by an axial compression of the portion intermediate the connected ends would amount to a deformed shape. Contrarily, a device 100 is considered to exist in an undeformed shape when any inherent bias forces have been overcome such that the device 100 assumes a shape commensurate with no net forces acting upon it, such as that associated with the linear (i.e., straight) sheath 110 of FIG. 7.

In another form (not shown) the control element 120 may be configured to have a tubular shape similar to sheath 110 in order to allow internal access through its lumen for additional component use. In either its solid (i.e., control wire 120) or hollow construction, such a control element 120 is sized to allow its longitudinal (or axial) placement within the sheath 110. In the case of where the control element 120 is itself of hollow construction, an operator may use additional devices that can be moved through or around the inner lumen of such control element 120.

As with the embodiment of FIGS. 4 through 6, a single helical line is shown in FIG. 7, extending from a starting cut or hole that is closer to the proximal end $110_P$ of the sheath 110 all the way until an end hole or cut near the distal end $110_D$ that culminates in tip 116. The pitch P may be made to vary over the axial dimension A such that farther away from the tip 116 the pitch $P_1$ is larger than the pitch $P_2$ that is closer to the tip 116. With such construction, the flexibility increases closer to the tip 116, while closer to the proximal end $110_P$ the bending properties of the sheath 110 are relatively similar to that of a non-slotted portion of the sheath 110. This variation in pitch P permits a gradual transition in flexibility in order to avoid undesired stress concentrations that otherwise may lead to failures. As the sheath 110 becomes compressed when a tension force is applied to the control wire 120, the sections of the wall 114 with smallest pitch $P_2$ will start bending first, and upon increasing axial force from the control wire 120, the amount of the sheath 110 that assumes a bent (rather than linear or straight) profile will increase until the most proximal section of slot 112 is finally closed that coincides with the maximum bending angle of sheath 110 being reached.

In yet another embodiment, the variable slot width features of FIGS. 4 through 6 may be combined with the variable pitch feature of FIG. 7. In that way, the slot 112 is in the shape of a helix with variable pitch P along the length of the sheath 110 and a variable slot width W along both (a) the helix defined by the slot 112 and (b) the sheath 110 that contains the helix. In both of the embodiments of FIGS. 4 through 6 and FIG. 7, the control element 120 may also be used with a preload in order to minimize the free tangential movement between adjacent sections of the helix that is formed in the sheath 110. As will be discussed in more detail below, there is another way to minimize the free tangential movement between adjacent helix sections through the use of locking members.

Referring next to FIGS. 8 and 9, details of the sheath 110 of the separate embodiments of FIGS. 4 through 6 and FIG. 7 are shown. Referring with particularity to FIG. 8, the shape of the slot 112 is enlarged in order to better see how the width W of slot 112 varies from one side (as shown, the top) to the other side (as shown, the bottom) of the sheath 110, changing from narrower width $W_1$ to wider width $W_2$. The length of a slot, starting at point B and running over 360 degrees until it reaches point Y, is determined by the diameter D and the pitch P of sheath 110. If both the pitch P and diameter D are constant, all locations where the wider width $W_2$ is present can be made to extend on a straight line along a common circumferential location of sheath 110. Referring with particularity to FIG. 9, a cross section of the sheath 110 with the top points T and bottom points B, as well as overlap points Y, $Y_1$ and $Y_2$. If all points Y correspond with B, the curvature of the sheath 110 upon actuation by the control wire 120 will be in one plane, with the concave side below. However, it is also possible to form the cuts in slot 112 in such a way that the widest portion of the loop of the slot starting at B does not end in Y, but in $Y_1$, and the widest portion of the next loop thereafter ends in $Y_2$, and so on. In such case, the actuated sheath 110 can obtain bending or curvature in more than one plane, such as that associated with a pig-tail shape. This helps promote a self-anchoring effect by providing a more complete contact between the sheath 110 and the wall of the lumen into which it is placed.

Figure 12:
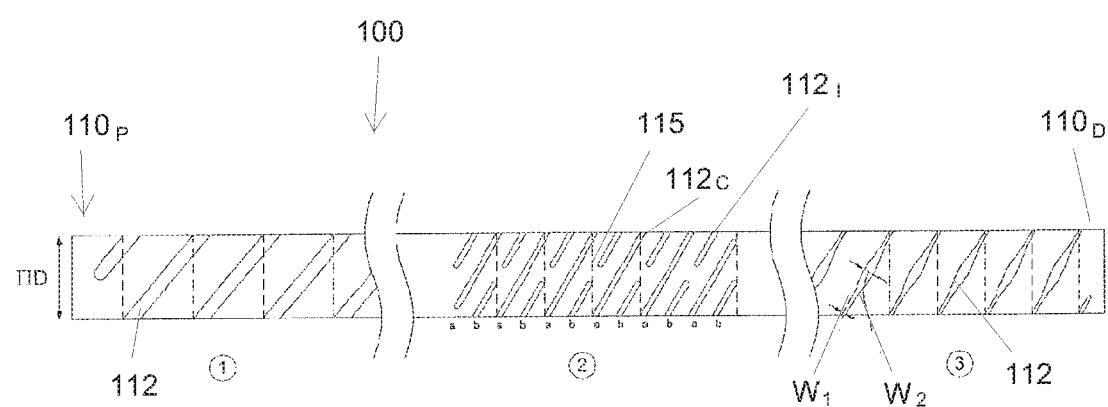
FIG. 12 shows a perspective view of a portion of a helically-slotted tubular sheath portion of a guide wire assembly according to another embodiment of the present disclosure.

Referring next to FIG. 12, a two-dimensional representation of an unraveled tubular sheath 100 that can be used as part of a steerable device, medical device or guide wire assembly according to one or more of the embodiments of the present disclosure is shown with three distinct regions the last two of which (regions 2 and 3) show how the reconfigurable section of the sheath 110 may be made up of two or more reconfigurable sections. The unraveled view is used to better show how the diameter D and entire circumference πD of the sheath 100 cooperate to provide one or more slot 112 patterns. Region 1 defines a proximal zone with a helical cut that is wide enough to make this section work as a compression spring; this zone generally corresponds to the proximal end $110_P$ of sheath 110. Region 2 is an example of slots 112 configured as a double helix, in this case a continuous helical slot $112_C$ and an interrupted helical slot $112_I$ in-between; this region may be used to increase the flexibility of device 100, as well as to create bending upon tension. In particular, the discontinuous nature of the interrupted helical slot $112_1$ acts to provide hinges 115 bridges or related landed areas (as will be discussed in more detail with FIGS. 14 and 15 below) that are created where the cuts that make up the slots 112 are interrupted. This has the effect of creating an asymmetrical rigidity when the hinges 115 are located on a common circumferential spot along the length of the sheath 110, such as when aligned in a row. Although only two helices are shown in the figure, more than two may be used as well, depending on the desired device 100 behavior. Region 3 shows the steerable distal end $110_D$ that may exhibit bending behavior upon applied tensile force such as that of a guide wire or related elongate control element (not presently shown). In a manner similar to that depicted in FIGS. 4 through 6, the variable slot width $W_1$ and $W_2$ around the circumference contribute to such steerability, although it will be appreciated that the variable slot pitch of FIGS. 7, 14 and 15 may be used as well.

Figure 13:
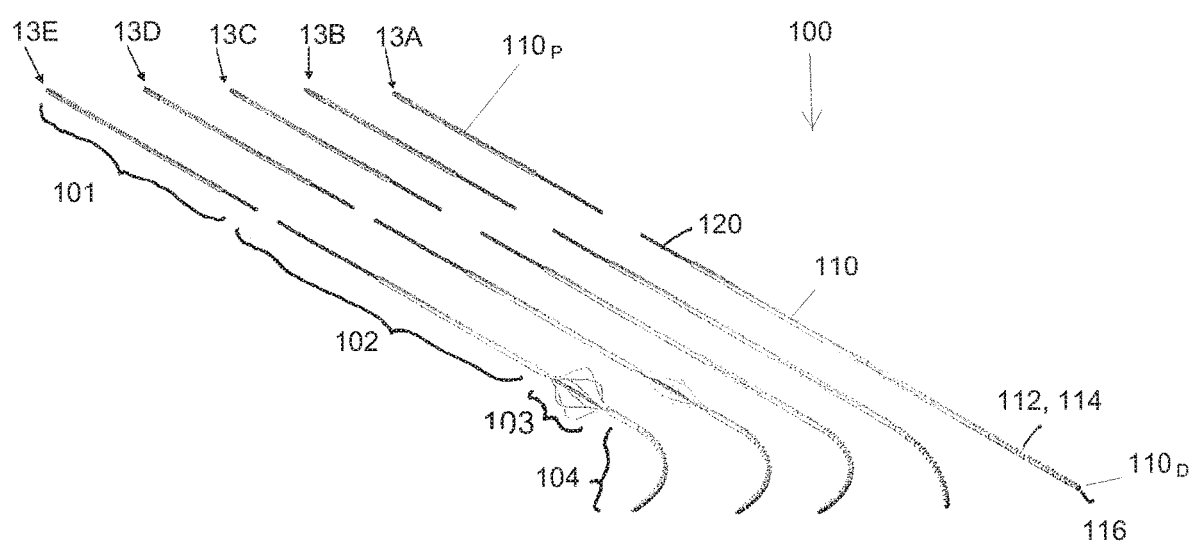
FIG. 13 shows five exploded views of a guide wire assembly in varying degrees of bending according to one or more of the embodiments of the present disclosure.

Referring next to FIG. 13, device 100 is shown in the form of a guide wire assembly as it exists in five different states of actuation from fully straight or linear at 13A through successively larger bends in 13B, 13C and 13D to bent at a 90 degree angle at 13E. The guide wire assembly includes an elastic bias section 101 where an operator (not shown) may manipulate the relative position between the control wire 120 and the sheath 110, an intermediate section 102 (shown with an indeterminant length), an anchoring section 103 that can be selectively expanded in order to establish secure contact between the device 100 and an interior lumen wall and a steerable section 104. Additional details associated with the construction of the guide wire assembly may be found in the aforementioned U.S. Pat. Nos. 7,776,062 and 8,382,786. In particular, the steerable section 104 may be made of one sheath 110 plus one control wire 120, connected to their respective two ends such as that shown for sheath proximal and distal ends $110_P$ and $110_D$. In the embodiment shown, the anchoring section 103 may be formed such that it is situated within the steerable section 104 to be a part thereof such that it is near the distal end $110_D$ of sheath 110. The elastic bias section 101 may be used as a tool such that when coupled to at least one of the control element 120 or the sheath 110, can be used to regulate relative axial positions between them to effect transitions in sheath 110 shape or rotation. Details associated with the elastic bias section 101 may be found in the aforementioned U.S. Pat. Nos. 7,776,062 and 8,383,786, and may further include a display configured to inform an operator about an operational status of the reconfigurable section that resides within the sheath 110. Although not shown, other features may be included at the distal end $110_D$ of sheath 110, including a steerable antenna or steerable drilling tool.

In both of the embodiments depicted in FIGS. 12 and 13, the reconfigurable section of sheath 110 may include a plurality of steerable sections (FIG. 12), as well as an expandable anchoring section 103 (FIG. 13) responsive to changes in force between the elongate control element 120 and the sheath 110. In particular, each of the steerable sections may be configured to be responsive to different levels in such force. Furthermore, these steerable sections may preferentially deform into similar shapes and directions, or do so independently of one another.

Referring next to FIG. 14, while the foregoing description pertains to a continuous slot 112 defining a single cut with variable width W that alternates between a smallest value $W_1$ and maximum value $W_2$, it is also possible to make $W_1$ zero. In particular, another embodiment of the device is shown as 200. Thus, rather than having one long continuous helical slot (such as that of FIGS. 4 through 11 and portions of FIG. 12), a series of discontinuous slots 212A, 212B, 212C, 212D and 212E may be formed in the sheath 210, while the control element 220 is substantially similar to that of the control element 120 discussed earlier. This would have the effect of providing a continuity in the wall 214 that forms a bridge, link or related hinge 215 between axially-adjacent wall sections. These hinges 215 act as short uncut sections that provide additional rigidity elements between adjacent wall 214 sections to prevent the full gap closure of the slot 212 between two wall 214 sections, while on the opposing side the gap can still be closed upon raising the tension in the actuating wire. Such a construction would provide improved torque resistance to help promote the one-to-one correspondence between each rotation at the proximal end $210_P$ and the distal end $210_D$, which in turn enhances the reliability of a particular steering movement. The upper portion of FIG. 14 shows an example of such an embodiment of the disclosure with a flat projection of the slot 212 cutting pattern via two-dimensional representation of the unraveled tubular sheath 200. The unraveled view is used to better show the relationship between the pitch P along the x-direction projection and the number of y-direction travels $\pi D$, $2\pi D$, $3\pi D$ . . . around the sheath 200 circumference, as well as how the helical slot angles relative to the axial dimension of the sheath 200 vary with the pitch P. In the lower portion of FIG. 14, opposing circumferential sides of a few helical slots 212 near the distal end are shown. As can be seen, the pitch P varies in a manner generally similar to that of the embodiment of FIG. 7. The length of a helical cut section will then also vary between a maximum length $L_1$ and a minimum length $L_5$.

The additional structural rigidity associated with devices 200 with such hinges 215 helps promote improved pushability, as well as prevent an undesirable torsional deviation of the sheath 210 between the proximal and distal ends $210_P$, $210_D$. As mentioned above, it is helpful to promote good and reliable steerability by ensuring that any rotation angle imparted to the proximal end produce an equal (i.e., one-to-one) rotation angle on the distal end. The hinges 215 further this one-to-one relationship by having the hinges 215 be aligned on the convex side (such as that depicted in FIG. 6) to prevent the axial shortening of the sheath 210 upon activation of the control wire 220, while the gap associated with the slots 212A, 212B, 212C, 212D and 212E on the opposing side enables such shortening. It will be appreciated that although presently shown as having the bending only taking place in one plane, the number and position of such hinges 215 can be chosen such that the bending can follow in either one plane or in several planes, and that all such variants are within the scope of the present disclosure.

As with the embodiments disclosed in FIGS. 4 through 6 and FIG. 7, the width W of the slots 212A, 212B, 212C, 212D and 212E may be variable or constant, depending on the application of the device 200. Similarly, the dimensions of the slots 212A, 212B, 212C, 212D and 212E close to their respective hinge 215 also defines the amount of hinge 215 deformation while the device 200 is being activated. As such, a very small slot width W close to the hinge 215 will prevent strong bending of the hinge 215 over an axis perpendicular to the longitudinal or axial dimension of the control element 220. Further, the ratio between diameter D and the slot width W on the concave side will determine the maximum amount of bending deformation of the hinge 215 around its longitudinal axis. As soon as the gaps between adjacent wall 214 sections on the concave side are entirely closed, additional sheath bending stops. In this position the device 200 not only reaches its maximum bending angle, but also become less floppy because of the full axial dimension contact of the slot 212 edges. This means that the rigidity of such devices 200 is controllable. Without tension in the control wire 220, the floppiness of the sheath 210 is optimal, while for increasing tension it gradually becomes stiffer. This stiffening starts in the sections where the pitch P is smallest, because these sections will elastically deform easier than sections with a larger pitch P. Increasing tension will thus cause a stiffening of the sheath 210 over an increasing length, combined with the increasing bending.

Referring next to FIGS. 15 and 16A-D, a variation of the embodiment of FIG. 14 is shown where rather than the hinges 215 of FIG. 14, a series of interlocking members 315 made up of complementary-shaped male and female sections with nesting capability are provided. In a preferred form, the width of the cut is made as small as possible in order to get a proper shape fit, while the remainder of the width W of the helical slot 312 is larger in order to prevent gap closure of the gap on the circumferentially opposing surface that would in turn cause inadvertent sheath 300 bending. In particular, a shortening of the section of the sheath 310 that includes the interlocking members causes a closure of the gap around the locking members, resulting in an increased tangential torsional rigidity of the section. As can be seen, the shape of the interlocking members 315 produces a corresponding variable shape within the portion of the slot 312 that is occupied by the interlocking members 315.

Reductions in tangential free movement or play may also be achieved through the use of locking members 315 such as those attached or integrally-formed between adjacent walls 314 that define a given slot 312; such locking improves the steerability and such locking members may also be used for devices without a helical cut. Another feature is the fact that applying tension to the central control element 320 automatically causes a minor tangential rotation between adjacent helical coils. This effect can eliminate the use of proximal rotation for steering the distal end. In the embodiments depicted in FIGS. 14 and 15, the control elements 220, 320 may—in addition to being used in a tension mode—be used in a pushing mode as a way to achieve one or both of a desired bending and STT effect.

The interlocking members 315 of FIG. 15 give more sheath 310 flexibility compared to those in FIG. 14, while the interlocking turns still enable a good rotational torqueability, although not as much as that of FIG. 14, because each interlocking member 315 still permits minor tangential direction rotation upon torsion. This rotation may be small for one loop of slot 312, but having as many as twenty or more loops within a sheath 310 will add up rapidly and leads to a relatively reduced degree of torqueability. Minimizing the gap around the interlocking member 315 is important in order to reduce the relative axial rotation between adjacent loops.

Referring next to FIGS. 16A through 16D, minimizing the gap discussed in conjunction with the interlocking members 315 of FIG. 15 is shown. When a specific tension force is applied to the control wire, the small V-shaped gap in slot 312 between the top of a male section and the bottom of the surrounding female section will close entirely. Thus, this application of a tension preload on the control element 320 of FIG. 15 can be used to control the tangential gap between the adjacent wall components. With a proper load there is full contact in the interlocking member 315 to promote torsional actuation at the proximal side into comparable one-to-one movement into the sheath 310 distal end.

Figure 16A:
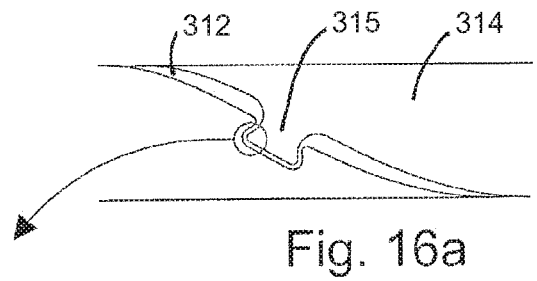
FIGS. 16A through 16D show details associated with a locking mechanism of the embodiment of FIG. 15.
Figure 16B:
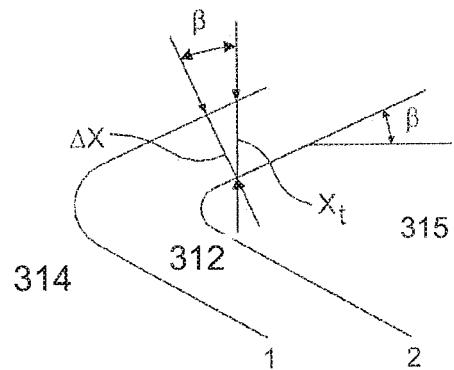
Figure 16C:
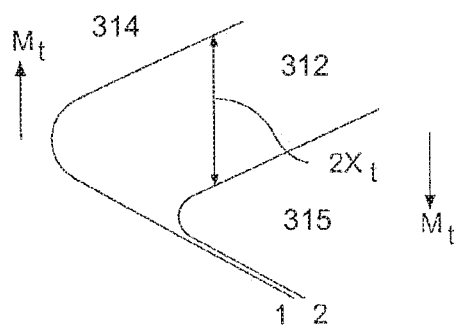
Figure 16D:
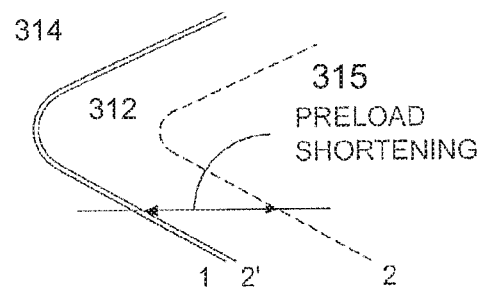

Examples of the function of the V-shaped gap 312 are shown. FIG. 16A shows with particularity a section of a sheath 310 with the gap of slot 312 around an interlocking member 315. The two borders of the gap are shown as $312_1$ and $312_2$. FIGS. 16B through 16D show enlargement details of FIG. 16A. In FIG. 16B, the angle between the gap of slot 312 with width $\Delta X$ and the length axis of the sheath 310 is given as $\beta$. As such, $\cos \beta = \Delta X / Xt$. Likewise, the tangential gap Xt can be described by the following formula:

$$Xt = \Delta X / \cos \beta.$$

FIG. 16C shows the same section after a moment of torque n is applied to the proximal side of the sheath 310 and if the distal end cannot freely rotate, the width of the gap first has to become zero before the full torque can be transferred from proximal to the distal side. Seen in the tangential direction this means that between each pair of adjacent slot 312 coils the rotation over a gap with a value of Xt is needed before real contact is made between surfaces $312_1$ and $312_2$ at which time a one-to-one torque can be applied. Each pair of coils causes an angular deviation $\phi$ in a sheath 310 with diameter D, which can be calculated as follows:

$$\phi = (Xt/\pi D) = \Delta X/(\pi D \cos \beta).$$

For example if $\beta = 60$ degrees and $D = 350$ microns and $\Delta X = 20$ microns, the deviation per coil $\phi = 2.20/(\pi 350) = 13$ degrees. This deviation will double if the torque direction is reversed, because the opposing gap between surfaces $312_1$ and $312_2$ has then reached a double width, as can be seen in FIG. 16C. It will be appreciated the otherwise desirable one-to-one steerability in response to applied torque is not desired in such cases, especially those involving when the direction of the applied torque has to be changed during device 300 steering. Nevertheless, by choosing a proper design of the interlocking member 315 and if a preload is applied which closes the tangential gap, the torsional steerability suddenly improves significantly, as can be seen in FIG. 16D. Here the gap between surfaces $312_1$ and $312_2$ is fully closed after applying the axial preload, where surface $312_2$ has now moved until its position depicted as $312_2$, where full contact is established. Of course this preload causes a decrease in the axial length with an amount of shortening of $\Delta X$, which in this example is slightly over 20 microns, but the influence is a lot less important than the gain in torsional steerability. For a sheath 310 made up of thirty coils, the total length would change only just over 600 microns, while the tangential deviation by torsional load is reduced significantly. For example, if the angular deviation $\phi$ in sheath 310 is 13 degrees per coil, then thirty coils would produce 390 degrees, while after applying the preload the deviation becomes zero. If the preload is chosen well, it has no influence on the straightness of the sheath 310. For clarity, it must be stated that the application of the preload for improving the torsional steerability is different than the final application for steering of the bendable distal end. Upon further increasing the axial preload the device will start bending because the opposing larger gaps on the convex side will start closing. Full release of the entire preload will result in an optimized floppiness of the slotted distal sheath 310 section, so the device has many features integrated into a single cutting design.

Although in the figures only a single row of interlocking members 315 is shown, it may be clear that more locking members, eventually in different planes may be used in order to improve certain aspects of devices according to the disclosure. For example, suppose that only tangential torquability is an issue and steerability is not important. In such cases the feature of closing the tangential gap of interlocking members 315 by axial preload is already a major issue and is an important claimed embodiment of the disclosure.

Of course the concept of closing the tangential gap not only works upon axial shortening. It may be clear that if the central control element 320 is used in a pushing mode, the interlocking members 315 can also be closed in a similar way as described above, but now upon lengthening. Further pushing enlarges the opposing gap in devices like the one of FIG. 15 and will also cause bending. It will be dependent on the type of application which choice is made, either pulling or pushing.

Instead of leaving small bridges or interlocking members in the sheath 310 material itself, as mentioned above, additional small rigidity elements (not shown) may be used to connect adjacent loops in a similar way, thus causing bending upon tension and preventing the relative torsional displacement between adjacent loops. In one form, the rigidity element is a polymer, glue or related material that fills the gaps and resists change of lengths and tangential shear between adjacent coils. Consistent with the discussion associated with FIGS. 4 through 6 above, this resistance against compression has to be higher at the convex side than on the concave side. In another example, a polymer cover (not shown) may be applied on the outer surface of the sheath 310. The polymer cover preferably has a wall thickness that is larger on the convex side than on the concave side. As such, the polymer cover would enable the bending of the sheath 310 while preventing tangential deviations between adjacent slot 312 loops caused by torque. There is no difference between the angle of rotation on the proximal end relative to the distal end, so the polymer cover has a similar function as the locking elements as described in FIGS. 15 and 16A through D.

Another possibility is the use of an eccentric reinforcement sheath (not shown), acting as a flexible spine, which is embedded in a layer around the sheath 310. This connection between this flexible section and the sheath 310 of the steerable device 300 may be achieved by any known technique, including the use of dipping, extrusion, welding, crimping, brazing, gluing or embedding in a surrounding cover material.

If additional flexibility is needed there may be extra slots besides the main helical slot. One example is that there are two or more continuous helical main slots. This would reduce the risk of failure, because if one section would break, the remainder of the helices would still keep the device intact, at least for a safe retrieval. In another embodiment of the disclosure there is one continuous main helical slot, while additional slots are each only located at the concave side and only run over an angle of less than 360 degrees. They can run with the same pitch angle as the continuous main slot or eventually with a different pitch angle. The advantage of such a series of interrupted extra slots is that they will also contribute to the steerability by bending, even if the main helix and additional have a constant slot width around the circumference. This is because there would be more slots on the concave side than on the convex side.

Besides the method of cutting slots in a sheath 110, 210, 310, there is also the possibility to form a strip of material into an elongate helical coil. By giving the strip an alternating width before it is formed into a helical coil. The distance between the widest parts of the strip determines the diameter of the final product. If the widest parts are exactly located on one side of the final coil, it will become a bending behavior in one plane, with the concave side being the opposing side. Of course other relative locations of the widest parts give different bending characteristics, like in more than one plane.

As mentioned throughout this disclosure, the need for a good one-to-one relationship between applied torque and sheath rotation is a significant limitation with devices employing conventional helical slots. While the various embodiments disclosed herein are made in such a way that any tangential deviation between adjacent coils is avoided as much as possible, another feature of the helical devices disclosed herein is the fact that applying tension to the central control element automatically causes a minor tangential rotation between adjacent helical coils or wall sections. As discussed above, a helical section that rotates tangentially around its own length axis by applying a length change in the helical wall corresponds to the STT; this effect can eliminate the need to apply proximal end rotation in order to produce sheath distal end steering, and in fact the prototypes discussed below take advantage of the STT effect. When there are enough coils available in the distal end the application of a tension force can cause a full tangential rotation of 360 degrees at the distal tip, while the major length of the guide wire is kept still. As will be understood by reference to the present disclosure, it is not required that STT be located at the very distal end of the device. For example, it may be also arranged either closer to the proximal end or somewhere in between the proximal and distal ends. In one embodiment a steerable bending tip may be combined with the STT. Another embodiment is with the STT section located more distally than the bending section, so that the torque effect appears under an angle with the proximal main length axis. Any combination between existing devices with the features of this disclosure, including one or more of the STT effect and the steerable sections, is deemed to be within the scope of the present disclosure.

This STT feature is particularly beneficial for very small diameter devices (such as devices used to navigate a body lumen) where the floppiness of extremely thin guide wires would otherwise inhibit the desirable one-to-one remote torque steering by rotating the proximal end around its length axis. Another advantage is that the operator does not have to rotate the entire wire together with its proximal manipulation tool, so it becomes easier to handle. The only need is a small knob for related tool (such as an elastic bias device) or applying some tension or the use of a proximal bias spring as described in U.S. Pat. Nos. 7,776,062 and 8,382,786.

Still another advantage of the STT principle is that the issue of friction becomes less critical as compared to devices using one-to-one torque. While the remainder of the device is kept still, the tip can be bent and rotated on its own, so the friction is significantly minimized. The operator only has to use the knob on the control element by pulling or pushing. Thus, once the tip is brought in the right position in front of a target lumen, it can just be pushed longitudinally farther into that lumen so that the procedure can be repeated as desired. This also means, if proximal torque is not needed anymore for steering, that the major length of the device may be made stiffer without losing the STT and steerability at the distal end.

Upon applying tension on the control element, the extreme floppiness of the helical distal end is reduced and it becomes more robust in order to enable the operator to push it forward into side branches of the lumen. After this branch is reached the distal end can be made floppy again, just by reducing the tension of the control element. Therefore the floppiness and shape of the distal end can be remote controlled.

While in this description the device is discussed in conjunction with a guide wire assembly, it should be clear that any device using one or more of the described features is meant to be part of the disclosure. The guide wire assembly is just one example out of many embodiments. The author of the present disclosure made some prototypes from a superelastic nitinol sheath with outer diameter of 0.34 mm and a wall thickness of 0.048 mm. A laser was used to cut a helical slot with a width of 0.060 mm into the wall with a pitch of 0.8 mm and with forty coils. Application of a tension force on a central steel wire with a diameter of 0.130 mm caused a tangential rotation at the distal end of 360 degrees, and the total shortening was 2.4 mm. So the tangential rotation was 9 degrees per coil. This prototype did not have a variable slot width.

Another sample was made in a superelastic nitinol tube with outer diameter of 0.34 mm and a wall thickness of 0.048 mm, and generally resembles according to FIG. 15, with the slot around the lock only 10 microns wide and 30 microns on the opposing side. The pitch of the coil was 0.5 mm for the twenty most distal coils and went over into a pitch of 0.8 mm for another twelve coils and finally into ten coils with a pitch of 1 mm. All locking members were located in one line parallel to the axial dimension of the sheath. Upon tension of a steel wire with diameter 0.076 mm a combined movement of the tip occurred. Initially, the tip starts bending, after which upon increasing tension the bent tip also rotates around the main length axis of the remainder of the uncut section. Moreover, the locking members all become engaged and the floppiness of the distal section disappears. Also the minor tangential rotation per coil, combined with the different slot width on opposing sides, makes that the device does not exactly bend in one plane, but in more planes, for example into a pigtail-like shape. If this is not desirable, the width of the slots may be modified and/or the slots may be placed with a small longitudinal offset per coil, which eventually be used to compensate the tangential rotation. Unlike the previously-described prototype, the presence of interlocking members evidences one form of the variable-width slot was included in this prototype.

The locking members ensure that during the STT-effect the wall of the helix is not deformed too strong and the outer surface remains in a smooth state. The locking members also ensure that the maximum tangential rotation upon tension is known and limited, so this information can be used in exact position control.

Another possibility to ensure that only pure tangential rotation appears is the use of an internal or external straight guiding member, which has a size that allows the free tangential rotation but prevents bending. In one prototype a stainless steel tube with outer diameter surrounds the control element with outer diameter 0.076 mm and they are both located in the nitinol tube that was mentioned above. Only the twenty most distal coils were not internally supported by stainless steel tube. Upon applying tension to the control element the distal twenty coils start bending first, because they have the smallest pitch. When the tension is further increased the coils with larger pitch will try to start bending, but also start to show the STT effect. As the internal supporting tube prevents bending for these coils, only the STT effect is apparent. The total result is that the most distal tip bends and then the STT causes this bent tip to rotate, enabling the operator to search the right position for reaching any branching side lumen with only the help of variable tension, without using proximal torque.

It may be clear that the same pure STT-effect can also be achieved by supporting the slotted helical section with a surrounding tube in which the device can freely rotate, while bending is prevented. The supporting tube does not have to be straight in all cases. In specific embodiments the supporting element may be curved in order to use the STT effect under an angle with the main proximal length axis, for example any angle between 0 and 180 degrees.

The supporting tube may be integrated with the most distal tension wire that functions as control element for the bending tip. Such an integrated element does not have to be made of separate tube and wire, but can for example be centre-less grinded into one piece of wire. Near the distal end flexibility upon bending is crucial, while prevention of bending in the STT section asks for a larger size of this element. Also closer to the proximal end the control element may be made thinner in order to make the proximal section more flexible. Only where the STT section is active, more support may be needed.

While the present disclosure emphasizes a device for guide wire applications, it will be appreciated by those skilled in the art that but the same principle can be used for a range of different exoluminal or endoluminal applications, including catheters, steerable tips, endoscopes, laser systems, ablation systems, stents, filters, angioplasty balloons, drains, dilators, filters, baskets, filterbaskets, anchors, floating anchors, occlusion devices, guide wires, stylets, electrodes, leads, drains, catheter sheaths for use with catheter introducers or a drug infusion catheter, or related medical devices. Likewise, the device 100 may further include one or more endoluminal devices that can slidably fit over the sheath, at least when the sheath is in the substantially undeformed second shape. The endoluminal device can be at least any of a catheter, steerable tip, endoscope, stent, filter, angioplasty balloon, drain, dilator, filter, basket, filterbasket, anchor, floating anchor, occlusion device, guide wire, stylet, electrode, lead, drain, catheter sheath for use with catheter introducers or a drug infusion catheter, as well as combinations of the above. Similarly, the device itself may be a catheter, steerable tip, stent, filter, angioplasty balloon, drain, dilator, basket, filterbasket, anchor, floating anchor, occlusion device, guide wire, stylet, electrode, lead, drain, catheter sheath for use with catheter introducers or a drug infusion catheter, or combination of the above. Furthermore, materials making up the control element and sheath can be made from polymers, metals or similar structural constituents, or combinations thereof. In a particular form, the metal can be a shape-memory metal. These materials are especially valuable for applications requiring reconfigurable or related components.

As mentioned above, the devices disclosed herein may be used in non-medical applications as well as medical applications. For devices using the principles according to the disclosure that are used in other fields than medical, different sizes and different techniques for providing the slots may be used. Examples are water jet cutting, etching, abrasive cutting and others. In another embodiment, there is no cutting of slots, for example if a technique such as 3-dimensional printing is used to form the device with an integrated pattern of slots. In another form of the device, steerable pipes may be used in oil wells, water wells, gas wells or the like, as well as for space applications or transportation systems. In yet another form, the devices may be configured as an endoscope for medical and non-medical use.

In general, it is advantageous if the distal end of a guide wire assembly is relatively compliant or floppy, while the majority of the length should be kink resistant, pushable, bendable and able to transmit torsional forces from the proximal to distal end in order to maneuver the assembly accurately. The tubular sheath can be chosen from any wire or hypotube material suitable for guide wire or catheter applications. One specifically suitable material is superelastic nitinol, a nickel-titanium alloy with shape-memory properties that is well-known for its flexibility, pushability, biocompatibility and kink resistance. In one configuration, the majority of the length of the tubular sheath may made of metal while the distal section may be made from a relatively soft and flexible material that easily deforms when the control wire being moved causes an axial compression in the tubular sheath. The control wire can be made of a high strength yet flexible polymer. If improved visibility for MRI or related radio-opacity is needed, additional markers of materials like gold, platinum, silver, tungsten, iridium or the like may be used at specific locations on either the control wire or the tubular sheath. Other material choices include metals and related materials for improved strength, stiffness or visibility for MRI or radio-opacity. Nitinol does not have to be in its superelasic mode, but can also be used in its linear elastic state, caused by a different thermomechanical production process.

The elastic bias section is disposed proximal relative to the reconfigurable section, and is configured to vary the axial length of the sheath's reconfigurable section, which in turn may be used to produce the variation in one or both of bending and rotation as discussed herein. The elastic bias section assists in compensating the relative movement between the control element and the sheath in the reconfigurable section by allowing relative movement of the sheath and the control element in the vicinity of the proximal end of the device. To achieve this, the elastic bias section acts as a bias spring to create an axial force necessary to keep the reconfigurable section in its deformed state. Actuation (such as by a user or operator) of the bias spring will cause a release of the axial force on the control element and so allow the spontaneous return of one or both of the anchoring and steerable sections from a deformed shape to an undeformed or lesser deformed shape.

For a proper functioning of all devices 100, 200, 300 described above it may be necessary to take precautions that the control elements 120, 220, 320 and respective steerable sheaths 110, 210, 310 always remain substantially concentric. This can be achieved by placing a flexible liner (not shown) in between the control elements 120, 220, 320 and their respective sheaths 110, 210, 310. In other cases, such a liner may be eccentric for achieving a different predictable behavior of the devices 100, 200, 300.

It is within the scope of the invention that any material or any combination of materials can be used in any configuration. For example, materials making up the elongate control elements 120, 220, 320 may include polymers (including high-strength polymers), metal and metal with enhanced radio-opacity (including magnetic resonance imaging) features. It will be appreciated by those skilled in the art that the control elements 120, 220, 320 may be made from a different material than the elongate tubular sheaths 110, 210, 310.

There are several options to making steerable devices according to the invention. Moreover, it is an object of the present disclosure that devices 100, 200, 300 discussed herein may be used in medical procedures, comprising minimal invasive devices, surgical tools, steerable drilling tools, instruments, rotating instruments, placement of pacemaker leads and implants. Of course it is also an object of the present disclosure that such devices 100, 200, 300 may be used in non-medical procedures, including but not limited to exploration, completion and maintenance of oil, gas and water wells, fluid and gas transport systems, manipulators in robotics, vacuum environments, laboratory equipment and other fields. Even for the use outside of a lumen the steerable devices 100, 200, 300 according to the present disclosure may be used, for example in a robot arm or in a manipulator in outer space or under water, like a manipulator arm on a submarine. One example would be a steerable antenna for outer space applications. Other applications are the fine adjustment of parts in drones and related unmanned aerial vehicles, like for example fine adjustment of wing flaps, rudders or propeller blades.

The STT effect mentioned above can also be used in devices without using a proximal mechanical actuation. For example, in space, vacuum, water, gas or oilfield applications, there may be enough room in the device to put an actuator closer to the distal section where steering is needed. This actuator can apply the necessary force on the control element by using an electrical or hydraulic lead, running to the proximal end. The remote electric, magnetic or hydraulic actuator only needs a steering signal, which is converted into the necessary force to move the control element in order to change the shape of the reconfigurable section. If needed, a gear or lever may be used to enlarge the needed force.

It is noted that terms like "preferably", "generally" and "typically" are not utilized herein to limit the scope of the claimed disclosure or to imply that certain features are critical, essential, or even important to the structure or function of the claimed disclosure. Rather, these terms are merely intended to highlight alternative or additional features that may or may not be utilized in a particular embodiment of the present disclosure. Likewise, for the purposes of describing and defining the present disclosure, it is noted that the terms "substantially" and "approximately" and their variants are utilized herein to represent the inherent degree of uncertainty that may be attributed to any quantitative comparison, value, measurement or other representation, as well as to represent the degree by which a quantitative representation may vary without resulting in a change in the basic function of the subject matter at issue.

While certain representative embodiments and details have been shown for purposes of illustrating the disclosure, it will be apparent to those skilled in the art that various changes may be made without departing from the scope of the disclosure, which is defined in the appended claims.

The invention claimed is:
1. A steerable device comprising:
 a tubular sheath comprising:
  a proximal end;
  a distal end opposite the proximal end; and
  at least one reconfigurable section disposed intermediate the proximal and distal ends and possessive of an increased flexibility through at least one helical slot formed through the wall thereof, the at least one helical slot of the tubular sheath defining:
   a pitch along a device axial dimension; and
   a pattern with a variable shape along the device axial dimension; and
 at least one control element defining a proximal end and a distal end, the at least one control element attached to at least one part of the tubular sheath in order to enable an operator to impose a force to the at least one control element that also causes a relative tangential movement between adjacent wall sections that define the at least one helical slot of the tubular sheath such that the imposed force results in a known, limited, controllable torsional rotation of the distal end of the tubular sheath without substantial torsional rotation of the proximal end of the tubular sheath.

2. The device of claim 1, wherein the at least one control element further defines a tubular profile comprising at least one reconfigurable section disposed intermediate the proximal and distal ends and that is possessive of an increased flexibility through at least one helical slot formed through the wall thereof, the at least one helical slot of the at least one control element defining:
a pitch along the device axial dimension; and
a pattern with a variable shape along the device axial dimension.

3. The device of claim 2, wherein the at least one helical slot of the at least one control element has a different orientation than the at least one helical slot of the tubular sheath such that a tangential movement is produced for the common distal end in the same direction when the at least one control element imparts a force to the tubular sheath.

4. The device of claim 2, further comprising an endoluminal device configured to slidably fit through the at least one control element.

5. The device of claim 2, wherein the pattern with a variable shape of the reconfigurable section of at least one of the tubular sheath or the at least one control element comprises a slot with a periodically-varying width configured such that a change in length of at least one of the tubular sheath or the at least one control element causes at least one of distal end bending, improved pushability, improved torquability or reduced flexibility therein.

6. The device of claim 5, wherein the periodically-varying width comprises at least one of (a) interlocking members having a nesting shape fit and (b) interruptions that define at least one tangential torsional rigidity-enhancing hinge in the at least one helical slot of at least one of the tubular sheath or the at least one control element.

7. The device of claim 6, wherein the slot width around the interlocking members is smaller than on the circumferential opposing side where no interlocking members are present.

8. The device of claim 2, wherein the pattern with a variable shape of the reconfigurable section of at least one of the tubular sheath or the at least one control element comprises a slot with a variable pitch configured such that a change in length of at least one of the tubular sheath or the at least one control element causes at least one of distal end bending, improved pushability, improved torquability or reduced flexibility therein.

9. The device of claim 2, further comprising a tool coupled to at least one of the at least one control element or the tubular sheath, the tool configured to regulate relative axial positions between the at least one control element and the tubular sheath and thereby effect a transition in the shape of at least one of the reconfigurable sections wherein such transition is selected from the group consisting of bending, reducing flexibility, improving pushability, locking to prevent torsion, active torsion by tension and combinations thereof.

10. The device of claim 2, wherein the pattern with a variable shape of the reconfigurable section of at least one of the tubular sheath or the at least one control element comprises a slot with a variable pitch configured such that a change in length of at least one of the tubular sheath or the at least one control element causes at least one of distal end bending, improved pushability, improved torquability or reduced flexibility therein.

11. The device of claim 1, wherein the pattern with a variable shape of the reconfigurable section of the tubular sheath comprises a slot with a periodically-varying width configured such that a change in length of the tubular sheath causes at least one of distal end bending, improved pushability, improved torquability or reduced flexibility therein.

12. The device of claim 11, wherein the periodically-varying width comprises at least one of (a) interlocking members having a nesting shape fit and (b) interruptions that define at least one tangential torsional rigidity-enhancing hinge in the at least one helical slot of the tubular sheath.

13. The device of claim 12, wherein the slot width around the interlocking members is smaller than on the circumferential opposing side where no interlocking members are present.

14. The device of claim 1, wherein the tubular sheath is provided with an elastic bias section cooperative with the sheath and wherein at least one part of the control element and the tubular sheath are fixedly attached to one another at their respective substantially opposing ends such that a tensile force imposed by the bias section in the tubular sheath on the at least one control element is sufficient to cause a relative tangential movement between adjacent wall sections within the at least one control element to produce a deformed first shape in the reconfigurable section of the at least one control element that may be overcome by application of a variation in the tensile force through movement of the elastic bias section such that the reconfigurable section assumes a second shape that has less tangential movement than the first shape.

15. The device of claim 1, wherein the at least one control element comprises:
a first control element attached to at least one part of the tubular sheath; and
a second control element attached to the first control element in order to enable an operator to vary the length of the distal end of the first control element by imposing a force thereto that effects a transition in the shape of at least one reconfigurable section formed within the first control element wherein such transition is selected from the group consisting of bending, reducing flexibility, improving pushability, locking to prevent torsion, active torsion by tension and combinations thereof.

16. The device of claim 1, wherein the device is selected from the group consisting of a steerable drilling tool, pipe, rotating instrument, robot arm, beam, antenna, manipulator and for endoluminal, minimal invasive devices, surgical tools, steerable drilling tools, instruments, rotating instruments, pacemaker and pacemaker lead implant tool, catheter tool, steerable tip for an endoscope, laser system, ablation system, stent, angioplasty balloon, drain, dilator, filter, basket, filterbasket, anchor, floating anchor, occlusion device, wire, guide wire, stylet, electrode, lead, catheter sheath for use with catheter introducers or a drug infusion catheter, and combinations thereof.

17. The device of claim 1, further comprising a rigidity element disposed between adjacent loops in the at least one helical slot of the tubular sheath in order to fill gaps formed therebetween and resist a change of length and tangential shear between the adjacent loops that arise due to relative torsional displacement between them.

18. The device of claim 1, wherein an eccentric reinforcement element is attached to the helical sheath by a technique selected from the group consisting of dipping, extrusion, welding, crimping, brazing, gluing and embedding in a cover material that is surrounding the sheath.

19. The device of claim 1, further comprising a remote controlled actuator that manipulates at least one of the tubular sheath or the at least one control element through at least one of a shape memory effect, hydraulic pressure, electric signal, magnetic signal, electromotor, direct action, lever action or mechanical gear box.

* * * * *

UNITED STATES PATENT AND TRADEMARK OFFICE
CERTIFICATE OF CORRECTION

| | |
|---|---|
| PATENT NO. | : 11,241,557 B2 |
| APPLICATION NO. | : 16/566342 |
| DATED | : February 8, 2022 |
| INVENTOR(S) | : Petrus A. Besselink |

It is certified that error appears in the above-identified patent and that said Letters Patent is hereby corrected as shown below:

In the Claims

Column 22, Line 15, Claim 13, "The device of claim 12, wherein" should read --The device of claim 2, wherein--.

Signed and Sealed this
Sixth Day of June, 2023

Katherine Kelly Vidal
*Director of the United States Patent and Trademark Office*